United States Patent [19]

Sandyk

[11] Patent Number: 5,691,325
[45] Date of Patent: *Nov. 25, 1997

[54] METHOD FOR AMELIORATING AGE-RELATED DISEASE CONDITIONS

[76] Inventor: Reuven Sandyk, 7 Piper Ct., Roslyn, N.Y. 11576

[*] Notice: The term of this patent shall not extend beyond the expiration date of Pat. No. 5,470,846.

[21] Appl. No.: 437,283

[22] Filed: May 8, 1995

Related U.S. Application Data

[63] Continuation-in-part of Ser. No. 181,677, Jan. 14, 1994, Pat. No. 5,470,846.
[51] Int. Cl.$^6$ .......... A61K 31/60; A61K 31/495; A61K 31/40; A61K 31/445
[52] U.S. Cl. .......... 514/159; 514/160; 514/250; 514/355; 514/345; 514/654; 514/419; 514/657
[58] Field of Search .......... 514/159, 160, 514/250, 355, 345, 654, 419, 657

[56] References Cited

U.S. PATENT DOCUMENTS

| | | | |
|---|---|---|---|
| 4,871,550 | 10/1989 | Millman | 424/601 |
| 5,157,031 | 10/1992 | Schwartz et al. | 514/177 |
| 5,340,568 | 8/1994 | Piazza et al. | 424/59 |

OTHER PUBLICATIONS

Lehninger et al., "Principles of Biochemistry," 2nd Ed., Worth Publishers, NY, 1993 pp. 341, 344, 886.
Scandalios, "Physiological Genetics", Academic Press, NY, 1979, pp. 40 & 41.
Physicians Desk Reference, 1989, pp. 625, 1003, 1004, 1701, 1702, 1881.
Physicians' Desk Reference for Nonprescription Drugs, 1991, pp. 584–586.

Primary Examiner—José G. Dees
Assistant Examiner—Mary C. Cebulak
Attorney, Agent, or Firm—Graham & James LLP

[57] ABSTRACT

A method of retarding the aging process and improving the symptoms of age-related disease conditions in humans which result from diminished pineal melatonin functions and reduced serotonin neurotransmission is described which comprises administering to a human in need thereof an effective amount of a composition which increases serotonin transmission to said human followed by the application to the brain of the human an effective amount of an AC pulsed magnetic field of proper intensity, frequency and waveform. Preferably the composition is supplemented by an effective amount of a dietary composition rich in the amino-acid tryptophan. Optionally an effective amount of an agent which provides growth hormone release is also administered prior to the application of the AC pulsed magnetic field. A composition useful for retarding the aging process and improving the symptoms of aging in humans which result from diminished pineal melatonin functions and reduced serotonin neurotransmission when administered to a human followed by the application to the brain of the human of an effective amount of an AC pulsed magnetic field of proper intensity, frequency and waveform, is described which composition comprises an effective amount of a composition which increases serotonin transmission to said human. Optionally, the composition can also include an effective amount of an agent which promotes growth hormone release.

39 Claims, 2 Drawing Sheets

METHOD FOR AMELIORATING AGE-RELATED DISEASE CONDITIONS

This is a continuation-in-part of my application Ser. No. 181,677 filed Jan. 14, 1994, now U.S. Pat. No. 5,470,846.

BACKGROUND OF THE INVENTION

The pineal gland is recognized as a neuroendocrine transducer, whose chief function is that of synchronizing endogenous circadian rhythms via the conversion of neuronal impulses to melatonin release. Aging is characterized by disorganization of circadian rhythms caused in part by the progressive decline in the activity of the pineal gland leading ultimately to pineal failure. The pineal gland is a magnetosensor organ and its functions can be enhanced by the external application of pulsed magnetic fields.

In my copending application Ser. No. 181,677, and my concurrently filed continuation-in-part thereof Ser. No. 08/437,273 filed May 5, 1995 (CIP-1), I described compositions and methods for treating neurological and mental disorders which are associated with and/or related pathogenetically to deficient serotonin neurotransmission and impaired pineal melatonin functions in humans.

These disorders which are associated with and/or related pathogenetically to impairment of pineal melatonin functions included multiple sclerosis, Parkinson's disease, dystonia, tardive dyskinesia, epilepsy, migraine, Alzheimer's disease, depression (including seasonal affective disorder and late luteal phase dysphoric disorder), schizophrenia, Gilles de la Tourette's syndrome, Attention deficit hyperactivity syndrome, anxiety and panic disorder, obsessive compulsive disorder, narcolepsy-cataplexy, myoclonus, akathisia and restless legs syndrome and chronic pain syndromes.

For many years physiologists considered the pineal gland, lodged deep within the brain, a vestigial organ which is merely an anatomical remnant of a primary sensory system. To the clinician the pineal gland, by virtue of its midline position and calcification, was of interest as a radiological landmark to identify intracranial space occupying processes. The pineal gland attracted scientific attention in 1963, when its primary secretion, melatonin, was first recognized as a hormone. Wurtman and Axelrod (1965) "The pineal gland." *Scientific American*, 231, 50–60) termed the pineal gland a "neuroendocrine transducer," an organ which converts neural signals from the external environment such as photic, acoustic, thermic, and magnetic cues into neuroendocrine output which acts on the nervous system largely via the secretion of its principal hormone melatonin.

The pineal gland is unique among endocrine organs for a number of reasons: (1) it is one of the few unpaired endocrine organs; (2) on a weight basis, it receives one of the richest blood supplies of any organ; (3) it lies outside the blood brain barrier, but has direct access to the cerebrospinal fluid (CSF) via the third ventricle; (4) it produces and/or contains high concentrations of a number of different indoleamines and low molecular weight peptides of probable endocrine importance; and (5) it is responsive to changes in magnetic field strength and to external electrical stimuli (Foley et al. (1986) "Pineal indoles: significance and measurement." *Neuroscience & Biobehavioral Reviews*, 10, 273–293).

Over the past several years scientists have come to suspect that melatonin is a "master hormone" involved in the control of circadian rhythms (biological cycles that recur at approximately 24-hour intervals), and protecting against common diseases of aging. Melatonin is now recognized to exert an important influence on a host of biological functions including synchronization of biological rhythms, stabilization of neuronal activity, regulation of sexual maturation and reproduction, immunomodulation, temperature control, sleep, mood, appetite, pain control, cognitive functions, and motor behavior (Ehrlich and Apuzzo (1985) "The pineal gland: anatomy, physiology, and clinical significance." *Journal of Neurosurgery*, 63, 321–341; Relkin (1966) "The pineal gland." *New England Journal of Medicine*, 274, 944–949; Reiter (1991) "Pineal melatonin: cell biology of its synthesis and of its physiological interactions." *Endocrine Reviews*, 12, 151–180; Datta and King (1980) "Melatonin: effects on brain and behavior." *Neuroscience & Biobehavioral Reviews*, 4, 451–458; Anton-Tay (1974) "Melatonin: effect on brain function." *Advances in Biochemical Psychopharmacology*, 11, 315–324; Cagnacci et al. (1994) "Melatonin-induced decrease of body temperature in women: a threshold event." *Neuroendocrinology*, 60, 549–552; Chuang et al. (1993) "Melatonin decreases brain serotonin release, arterial pressure and heart rate in rats." *Pharmacology*, 47, 91–97; Armstrong and Redman (1991) "Melatonin: a chronobiotic with antiaging properties?" *Medical Hypotheses*, 34, 300–309; Reiter (1992) "The ageing pineal gland and its physiological consequences." *BioEssays*, 14, 169–175; Trentini et al. (1991) "Pineal gland and aging." *Aging*, 3, 103–116; Drew and Bart (1972) "A contribution to the evolutionary theory of dreaming: an hypothesis on the role of the pineal gland in species and specimen protection." *Biological Psychiatry*, 4, 131–146; Bubenik and Pang (1994) "The role of serotonin and melatonin in gastrointestinal physiology: ontogeny, regulation of food intake, and mutual serotonin-melatonin feedback." *Journal of Pineal Research*, 16, 91–99).

In experimental animals pinealectomy (i.e., removal of the pineal gland) results in a syndrome of deficits which include disruption of circadian rhythms and sleep phases, facilitation of a narcoleptic-type REM sleep distribution, increased susceptibility to epileptic seizures, facilitation of abnormal orofacial involuntary movements, decreased tolerance to heat, impairment of opioid analgesia, reduction in brain neurotransmitter levels such as serotonin and GABA, delayed brain maturation, impaired electrolyte balance specifically sodium, calcium and phosphorus metabolism, arterial hypertension, increased plasma cortisol levels, disruption of adrenomedullary diurnal catecholamine synthesis, a biochemical diabetes-like state, elevation of blood cholesterol levels, disruption of circadian rhythms of gonadotropins and testosterone with resultant enlargement of the prostate, impaired wound healing, and promotion of cancer growth due to disruption of immunomodulation and reduced ability to protect cell membranes from peroxidative damage (Armstrong and Redman (1991) "Melatonin: a chronobiotic with antiaging properties?" *Medical Hypotheses*, 34, 300–309; Aldegunde et al. (1985) "Effects of pinealectomy on regional brain serotonin metabolism." *International Journal of Neuroscience*, 26, 9–13; Cunnane et al. (1979) "The pineal gland and regulation of fibrosis: pinealectomy as a model of primary biliary cirrhosis: roles of melatonin and prostaglandins in fibrosis and regulation of T lymphocytes." *Medical Hypotheses*, 5, 403–407; Kincl et al. (1970) "Observation on the influence of changing photoperiod on spontaneous wheelrunning activity of neonatally pinealectomized rats." *Endocrinology*, 87, 38–42; Banerji and Quay (1976) "Adrenal dopamine beta-hydroxylase activity: twenty four hour rhythmicity and evidence for pineal control." *Experientia*, 32, 253–255; Csaba and Barth (1974)

"The effect of pinealectomy on the perifollicular cells of the rat thyroid gland." *Acta Anatomica*, 88, 137–146; Kinson and Peat (1971) "The influences of illumination, melatonin and pinealectomy on testicular function in the rat." *Life Sciences*, 10, 259–269; Shirama et al. (1982) "Influence of pinealectomy on circadian patterns of plasma luteinizing hormone, follicle-stimulating hormone, testosterone and dihydrotestosterone in the male rat." *Journal of Endocrinological Investigations*, 5, 397–401; Milcu et al. (1971) "The effect of pinealectomy on plasma insulin in rats." In G. E. W. Wolstenholme and J. Knight (Eds.), *The pineal gland (pp. 345–360)*. London:Churchill Livingstone; Diaz and Blazquez (1986) "Effect of pinealectomy on plasma glucose, insulin and glucagon levels in the rat." *Hormone Metabolic Research*, 18, 225–229; Zanoboni and Zanoboni-Muciaccia (1967) "Experimental hypertension in pinealectomized rats." *Life Sciences*, 6, 2327–2331; Holmes and Sugden (1976) "The effect of melatonin on pinealectomy-induced hypertension in the rat." *British Journal of Pharmacology*, 56, 360–361; Karppanen et al. (1970) "Studies with pinealectomized rats." *Pharmacology*, 3, 76–84; Kavaliers et al. (1983) "Ageing, opioid analgesia and the pineal gland." *Life Sciences*, 32, 2279–2287; Kumar et al. (1982) "Diurnal fluctuations in methionine-enkephalin levels in the hypothalamus and preoptic area of the male rat: effects of pinealectomy." *Neuroendocrinology*, 35, 28–31; Nir et al. (1969) "Changes in the electrical activity of the brain following pinealectomy." *Neuroendocrinology*, 4, 122–127; Kamback et al. (1982) "Effect of pinealectomy on fatty acid composition of rat brain myelin." *Endocrinology*, 110, 907–909; Reiter et al. (1973) "Nature and time course of seizures associated with surgical removal of the pineal gland from parathyroidectomized rats." *Experimental Neurology*, 38, 386–397; Mouret et al. (1974) "Effet de la pinealectomie sur les etats et rythmes de sommeil du rat male." *Brain Research*, 81, 97–105; Oxenkrug et al. (1984) "Effects of pinealectomy and aging on the serum corticosterone circadian rhythm in rats." *Journal of Pineal Research*, 1, 181–185; Sandyk and Fisher (1989) "Increased incidence neuroleptic-induced movement disorders in pinealectomized rats." *International Journal of Neuroscience*, 48, 303–308; Heldmaier and Lynch (1986) "Pineal involvement in thermoregulation and acclimatization." *Pineal Research Reviews*, 4, 97–139; Pieri et al. (1994) "Melatonin:a peroxyl radical scavenger more effective than vitamin E." *Life Sciences*, 55, PL271–276; Lapin and Ebels (1981) "The role of the pineal gland in neuroendocrine control mechanisms of neoplastic growth." *Journal of Neural Transmission*, 50, 275–282; Romijn (1978) "The pineal a tranquillizing organ?" *Life Sciences*, 23, 2257–2274).

Many of the disease conditions associated with aging such as sleep and cognitive disorders, mental depression, disruption of the circadian rhythms of pituitary hormone secretion, obesity, hypertension, atherosclerosis, osteoporosis, hypercholesterolemia, glucose intolerance, ionic imbalance, endocrine changes (i.e., decrease plasma gonadotropin and growth hormone levels) and gastrointestinal disorders (i.e., bowel constipation), are thought to be related to or associated with the gradual decline in the secretory activity of the pineal gland with aging with resultant disorganization of circadian rhythms (Brown et al. (1979) "Melatonin in human cerebrospinal fluid in daytime; its origin and variation with age." *Life Sciences*, 25, 929–936; Iguchi et al. (1982) "Age-dependent reduction in serum melatonin concentrations in healthy human subjects." *Journal of Clinical Endocrinology and Metabolism*, 55, 27–29; Nair et al. (1986) "Plasma melatonin—an index of brain aging in humans?" *Biological Psychiatry*, 21, 141–150; Sack et al. (1986) "Human melatonin production decreases with age." *Journal of Pineal Research*, 3, 379–388; Sandyk et al. (1992) "Is postmenopausal osteoporosis related to pineal gland functions?" *International Journal of Neuroscience*, 62, 215–225; Birau (1981) "Melatonin in human serum: progress in screening investigation and clinic." In Birau N. and Shloot W. (Eds.), *Melatonin:current status and perspectives* (pp. 297–326). Oxford:Pergamon Press; Barnes et al. (1974) "Insulin resistance, skin changes, and virilization: a recessively inherited syndrome possibly due to pineal gland dysfunction." *Diabetologia*, 10, 285–289." Tasca et al. (1974) "Disappearance of aortic lesions in the rabbits with experimental atheromatosis after pineal extraction administration." *Revue Roumanian d'Endocrinologie*, 11, 209–213; Ostroumova and Vasiljeve (1976) "Effect of polypeptide pineal extract on fat-carbohydrate metabolism." *Problems in Endocrinology*, 22, 66–69; Muller-Wieland et al. (1994) "Melatonin inhibits LDL receptor activity and cholesterol synthesis in freshly isolated human mononuclear leukocytes." *Biochemical and Biophysical Research Communications*, 203, 416–421; Trentini et al. (1991) "Pineal gland and aging." *Aging*, 3 103–116; Grad and Rozencwaig (1993) "The role of melatonin and serotonin in aging:update." *Psychoneuroendocrinolgy*, 18, 283–295; Armstrong and Redman (1991) "Melatonin:a chronobiotic with antiaging properties?" *Medical Hypotheses*, 34, 300–309; Reuss et al. (1986) "Electrophysiological and endocrinological aspects of aging in the rat pineal gland." *Neuroendocrinology*, 43, 466–470; Thomas and Miles (1989) "Melatonin secretion and age." *Biological Psychiatry*, 25, 365–367; Wetterberg (1983) "The relationship between the pineal gland and the pituitary-adrenal axis in health, endocrine and psychiatric conditions." *Psychoneuroendocrinology*, 8, 75–80; Touitou et al. (1984) "Patterns of plasma melatonin with ageing and mental condition: stability of nyctohemeral rhythms and differences in seasonal vatriatons." *Acta Endocrinologica*, 106, 145–151; Copinschi and Van Cauter (1994) "Pituitary hormone secretion in aging: roles of circadian rhythmicity and sleep." *European Journal of Endocrinology*, 131, 441–442).

In fact, in recent years, melatonin has been considered an anti-aging hormone and the hypothesis has been put forward that aging is secondary to pineal failure (Walker et al. (1978) "Pineal gland structure and respiration as reflected by age and diet." *Experimental Gerontology*, 13, 91–99; Rozenchwaig et al. (1987) "The role of melatonin and serotonin in aging." *Medical Hypotheses*, 23, 337–352; Sandyk (1990) "Possible role of pineal melatonin in the mechanisms of aging." *International Journal of Neuroscience*, 52, 85–92; Grad and Rozencwaig (1993) "The role of melatonin and serotonin in aging:update." *Psychoneuroendocrinology*, 18, 283–295; Pierpaoli et al. (1990) "Aging-postponing effects of circadian melatonin: experimental evidence, significance and possible mechanisms." *International Journal of Neuroscience*, 51, 339–340; Pierpaoli (1991) "The pineal gland:a circadian or seasonal aging clock?" *Aging*, 3, 99–101; Lesnikov and Pierpaoli (1994) "Pineal cross transplantation (old-to-young and vice versa) as evidence for an endogenous "aging clock." *Annals of the New York Academy of Sciences*, 719, 456–460; Sharma et al. (1989) "Circadian rhythms of melatonin and cortisol in aging." *Biological Psychiatry*, 25, 305–319; Stokkan et al. (1991) "Food restriction retards aging of the pineal gland." *Brain Research*, 545, 66–72; Laudon et al. (1988) "Melatonin receptors in discrete brain areas of the male rat. Impact of aging on density and on circadian rhythmicity."

*Neuroendocrinology*, 48, 577–583; Reiter et al. (1980) "Pineal melatonin rhythm:reduction in aging syrian hamsters." *Science*, 210, 1372–1373). Moreover, it has been suggested that the pineal gland regulates the necessary genetic switching occurring in the cells throughout the body which cause the aging process (Kloeden et al. (1990) "Does a centralized clock for ageing exist?" *Gerontology*, 36, 314–322).

According to this hypothesis aging is a process related to melatonin deficiency as ablation of the pineal gland in rodents produced pathological changes resembling senescence which are reversed by the administration of a pineal extract or melatonin (Malm et al. (1959) "The effect of pinealectomy on bodily growth, survival rate and P32 uptake in the rat." *Acta Endocrinologica*, 30, 22–28; Dilman et al. (1979) "Increase in life span in rats following polypeptide pineal extract treatment." *Experimental Pathology*, 17, 539–545; Pierpaoli and Maestroni (1987) "Melatonin: a principal neuroimmunoregulatory and anti-stress hormone:its anti-aging effects." *Immunology Letters*, 16, 355–362). Moreover, senescence is also inhibited and life span is prolonged when the pineal glands of young mice are grafted into old animals (Pierpaoli et al. (1991) "The pineal control of aging: the effects of melatonin and pineal grafting on the survival of older mice." *Annals of the New York Academy of Sciences*, 621, 291–313; Pierpaoli and Regelson (1994) "Pineal control of aging: effect of melatonin and pineal grafting on aging mice." *Proceedings of the National Academy of Sciences, USA*, 91, 787–791; Walker et al. (1978) "Pineal gland structure and respiration as affected by age and hypocaloric diet." *Experimental Gerontology*, 13, 91–99).

One of the mechanisms by which melatonin acts as an antiaging hormone is through the promotion of the release of growth hormone (Martin (1976) "Pathophysiology of growth hormone regulation." In Martini and Ganong (Eds.), "*Frontiers in neuroendocrinology*" (pp. 129–168) New York:Raven Press; Smythe and Lazarus (1974) "Growth hormone responses to melatonin in man." *Science*, 1984, 1373; Petterborg et al. (1991) "Effect of melatonin replacement on serum hormone rhythms in a patient lacking endogenous melatonin." *Brain Research Bulletin*, 27, 181–185). Growth hormone secretion declines dramatically with aging accounting for several features associated with aging such as memory loss, obesity, decreased motor activity, increased incidence of sleep disturbances, and increased susceptibility to hypothermia (Plum and van Uitert (1978) "Nonendocrine diseases and disorders of the hypothalamus." In Reichlin et al. (Eds.), "*The Hypothalamus*" (pp. 415–473) New York:Raven Press; Finkelstein et al. (1972) "Age-related change in the twenty-four hour spontaneous secretion of growth hormone." *Journal of Clinical Endocrinology and Metabolism*, 35, 665–670; Carlson et al. (1972) "Absence of sleep related growth hormone peaks in aged normal subjects and in acromegaly." *Journal of Clinical Endocrinology and Metabolism* 34, 1102–1105; Van Coevorden et al. (1991) "Neuroendocrine rhythms and sleep in aging men." *American Journal of Physiology*, 260, E651–661).

The clinical consequences of melatonin deficiency include, among others, decrease in cerebral energy metabolism with decline in memory and other cognitive functions, tendency to depressive mood, decline in the percentage of alpha brain waves, deterioration of sleep efficiency with increased number of nocturnal awakenings, increased daytime sleepiness, diminished immune functions with increased probability of cancer and autoimmune diseases, deterioration of metabolic and endocrine homeostasis, impaired gastrointestinal motility, susceptibility to the development of psoriasis, acceleration of atherosclerosis, poor wound healing, and decreased longevity (Reiter, R. J. (1992) "The ageing pineal gland and its physiological consequences." *BioEssays*, 14, 169–175; Okawa et al. (1994) "Morning bright light therapy for sleep and behavior disorders in elderly patients with dementia." *Acta Psychiatrica Scandinavica*, 89, 1–7; Birau and Schloot (1979) "Pathological nyctohumeral rhythm of melatonin secretion in psoriasis." *IRCS Medical Science*, 7, 400; Lieberman (1986) "Behavior, sleep and melatonin." *Journal of Neural Transmission*, 21 (suppl), 233–241; Bartsch et al. (1981) "Urinary melatonin levels in human breast cancer patients." *Journal of Neural Transmission*, 52, 281–294; Tamarkin et al. (1982) "Decreased nocturnal plasma melatonin peak in patients with estrogen receptor positive breast cancer." *Science*, 216, 1003–1005; Haimov et al. (1994) "Sleep disorders and melatonin rhythms in elderly people." *British Medical Journal*, 309, 167; Miles and Philbrick (1988) "Melatonin and psychiatry." *Biological Psychiatry*, 23, 405–425; Pavel et al. (1980) "Vasotocin, melatonin and narcolepsy: possible involvement of the pineal gland in its pathophysiological mechanism." *Peptides*, 1, 281–284; Rozencwaig et al. (1987) "The role of melatonin and serotonin in aging." *Medical Hypotheses*, 23, 337–352; Armstrong and Redman (1991) "Melatonin: a chronobiotic with antiaging properties?" *Medical Hypotheses*, 34, 300–309).

Melatonin has been considered a chronobiotic hormone, i.e., a hormone that can act as a synchronizer or "Zeitgeber" to reset the phase of biological rhythms by acting on the circadian pacemaker in the suprachiasmatic nucleus of the hypothalamus (Armstrong and Redman (1991) "Melatonin: a chronobiotic with antiaging properties?" *Medical Hypotheses*, 34, 300–309). Consequently, diminished pineal melatonin functions may result in the disruption of biological rhythms of numerous biochemical, physiological, hormonal, and behavioral systems leading to disease and aging (Armstrong and Redman (1991) "Melatonin: a chronobiotic with anti-aging properties?" *Medical Hypotheses*, 34, 300–309; Ingram et al., (1982) "Circadian rhythmicity and sleep:effects of aging in laboratory animals." *Neurobiology of Aging*, 3, 287–297; Van Gool et al. (1987) "Age-related changes in circadian sleep-wakefullness rhythms in male rats isolated from time cues." *Brain Research*, 413, 384–387).

Since melatonin is a chronobiotic hormone it may be used therapeutically to re-entrain short-term dissociated or long-term desynchronized circadian rhythms or physiologically prevent their disruption following environmental insult and thus correct many of the pathological conditions which are associated with pineal failure associated with aging. For instance, the fact that melatonin administered to humans alleviates the deleterious effects of jet-lag, prolongs deep stages of sleep (i.e., restores youthful sleep patterns) and improves mood (Arendt et al. (1987) "Some effects of jet-lag and their alleviation by melatonin." *Ergonomics*, 30, 1379; Kales and Kales (1974) "Sleep disorders: recent findings in the diagnosis and treatment of disturbed sleep." *New England Journal of Medicine*, 290, 487–499; Haimov et al. (1994) "Sleep disorders and melatonin rhythms in elderly people." *British Medical Journal*, 309, 167) supports its chronobiotic properties as are the findings that bright light, which synchronizes biological rhythms, improves sleep and behavior disorders in the elderly and patients with Alzheimer's dementia (Okawa et al. (1994) "Morning bright light therapy for sleep and behavior disorders in elderly patients with dementia." *Acta Psychiatrica Scandinavica*, 89-1–7;

Satlin et al. (1992) "Bright light treatment of behavioral and sleep disturbances in patients with Alzheimer's disease." *American Journal of Psychiatry*, 149, 1028–1032) and the findings that melatonin extends the life span in experimental animals (Pierpaoli and Maestroni (1987) "Melatonin: a principal neuroimmunoregulatory and anti-stress hormone: its anti-aging effects." *Immunology Letters*, 16, 355–362; Pierpaoli and Regelson (1994) "Pineal control of aging: effect of melatonin and pineal grafting on aging mice." *Proceedings of the National Academy of Sciences, USA*, 91, 787–791).

I believe that one of the mechanisms by which melatonin acts as an anti-aging hormone is through the promotion of the release of growth hormone. Growth hormone is an anabolic hormone which stimulates protein synthesis, bone growth and glucose metabolism. In addition, it promotes inhibition of fat formation and causes improved sleep energy, enhancement of immune functions, and stimulation of nerve growth factors (Quabbe (1985) "Hypothalamic control of GH secretion:pathophysiology and clinical implications." *Acta Neurochirurgica*, 75, 60–71; Astrom and Trojaborg (1992) "Effect of growth hormone on human sleep energy." *Clinical Endocrinology*, 36, 241–245; Rusovan and Kanje (1992) "Magnetic fields stimulate peripheral nerve regeneration in hypophysectomized rats." *NeuroReport*, 3, 1039–1041). The secretion of growth hormone from the pituitary gland particularly during sleep declines gradually with aging thus accounting for several features associated with aging such as decreased protein synthesis, bone loss, decline in immune functions, decline in the activity of nerve growth factors, progressive memory loss, obesity, decreased motor activity, increased incidence of sleep disturbances and increased susceptibility to hypothermia (Meites (1986) "The neuro-endocrinology of hypothalamic aging." In Muller E. E. and MacLeod, R. M. (Eds.), *Neuroendocrine perspectives*, vol. 5 (pp. 179–189). Amsterdam: Elsevier; Plum and van Uitert (1978) "Nonendocrine diseases and disorders of the hypothalamus" In Reichlin et al. (Eds.), *"The hypothalamus"* (pp. 415–473) New York:Raven Press; Van Coevorden et al. (1991) "Neuroendocrine rhythms and sleep in aging men." *American Journal of Physiology*, 260, E651–661).

It is my belief based on my knowledge in the field, that the anti-aging effect of the pulsed magnetic field is enhanced by prior administrations of agents which promote growth hormone release. Thus my present invention additionally includes administering an effective amount of an agent which promotes growth hormone release prior to application of the AC pulsed magnetic field. The amino acids L-arginine and L-ornithine both stimulate the release of growth hormone in humans (Martin and Reichlin (1987) "Regulation of growth hormone secretion and its disorders" In *Clinical neuroendocrinology* (p. 237) F. A. Davis: Philadelphia).

In addition to the ambient light/dark cycle, the activity of the pineal gland and hence the rate of melatonin secretion is influenced also by the earth's geomagnetic field which is in the order of 30,000–60,000 nanotesla (0.3–0.6 Gauss). The earth's magnetic field is primarily a nontime-varying (DC) field with angle of incidence to the earth's surface increasing with increasing latitude. For comparison, anthropogenic magnetic fields are primarily time varying at 50 or 60 Hz and harmonic of these frequencies. Typical magnetic fields measured in residential settings range from 0.1 microtesla to 3 microtesla at 60 Hz frequency. The geomagnetic field has been a part of the environment throughout the evolution of animals and is used by certain species in their adaptive strategies. Organisms are capable of perceiving its intensity, polarity, and direction (Gould (1984) "Magnetic field sensitivity in animals." *Annual Review of Physiology*, 46, 585–598). It is thought that the circadian rhythmicity of the earth's magnetic field may have an additional "Zeitgeber" (time cue) function in the organization of biological rhythms (Cremer-Bartels et al. (1984) "Magnetic field of the earth as additional zeitgeber for endogenous rhythms?" *Naturwissenschaften*, 71, 567–574; Wever (1968) "Einfluss Schwacher Elektro-magnetischer Felder auf die Circadiane Periodik des Menschen." *Naturwissenschaften*, 55, 29–32; Bartsch et al. (1994) "Seasonality of pineal melatonin production in the rat: possible synchronization by the geomagnetic field." *Chronobiology International*, 11, 21–26).

Since the activity of the pineal gland is sensitive to the influences of the geomagnetic field it has been suggested that it functions as a magnetoreceptor as well (Semm et al.(1980) "Effects of an earth-strength magnetic field on electrical activity of pineal cells." *Nature*, 288, 607–608; Semm (1983) "Neurobiological investigations on the magnetic sensitivity of the pineal gland in rodents and pigeons." *Comparative Biochemistry and Physiology*, 76A, 683–689; Olcese et al. (1988) "Geomagnetic field detection in rodents." *Life Sciences*, 42, 605–613; Demaine and Semm (1985) "The avian pineal gland as an independent magnetic sensor." *Neuroscience Letters*, 62, 119–122; Rudolph et al. (1988) "Static magnetic fields decrease nocturnal pineal cAMP in the rat." *Brain Research*, 446, 159–160). Based on histological studies and electrophysiological single unit recordings from the pineal gland of rodents and pigeons, it has been estimated that 20%–30% of pineal cells respond to magnetic fields (Semm (1983) "Neurobiological investigations on the magnetic sensitivity of the pineal gland in rodents and pigeons." *Comparative Biochemistry and Physiology*, 76A, 683–689). Electrophysiological studies by Reuss et al. ((1983) "Different types of magnetically sensitive cells in the rat pineal gland" *Neuroscience Letters*, 40, 23–26) have demonstrated the presence of different types of magnetically sensitive cells in the pineal gland of the rat.

Furthermore, short-term exposure of experimental animals to magnetic fields of various intensities has been shown to alter temporarily the secretion of melatonin while more chronic exposure may even induce ultrastructural morphological changes in the pineal gland (Bardasano et al. (1985) "Ultrastructure of the pineal cells of the homing pigeon *Columba livia* and magnetic fields (first trials)." *Journal Fuer Hirnforschung*, 26, 471–475; Semm et al. (1980) "Effects of an earth-strength magnetic field on electrical activity of pineal cells." *Nature*, 288 607–608; Welker et al. (1983) "Effects of an artificial magnetic field on serotonin N-acetyltransferase activity and melatonin content of the rat pineal gland." *Experimental Brain Research* 50, 426–432; Wilson et al. (1981) "Neuroendocrine mediated effects of electromagnetic field exposure: possible role of the pineal gland." *Life Sciences*, 45, 1319–1332).

The human pineal gland, likewise, is believed to be sensitive to changes in the environmental magnetic fields. Howard et al. ((1965) "Psychiatric ward behaviour and geophysical parameters." *Nature*, 205, 1050–1052) made the seminal observations of a relationship between increased geomagnetic activity and the rate of admission of patients to psychiatric facilities. Rajaram and Mitra (1981) "Correlation between convulsive seizure and geomagnetic activity." *Neuroscience Letters*, 24, 187–191 and Venkatraman ((1976) "Epilepsy and solar activity. An hypothesis." *Neurology* (India), 24, 1–5) reported an association between changes in the geomagnetic field due to magnetic storms and frequency of seizures in epileptic patients. Semm (1992) "Pineal function in mammals and birds is altered by earth-strength magnetic fields." In Moore-Ede, Campbell, and Reiter (Eds.), *Electromagnetic Fields and Circadian Rhythmicity*, (pp. 53–62), Birkhauser: Boston) observed in normal subjects placed in the center of a Helmholtz coil system that inversion of the horizontal component of the ambient magnetic field for 30 minutes at midnight resulted in a significant (70%) depression of plasma melatonin concentrations.

In addition to melatonin and light, human circadian rhythms may be synchronized by magnetic fields. For instance, there is increasing evidence that the earth's magnetic field, which also undergoes diurnal and seasonal variations (Cremer-Bartels et al. (1984) "Magnetic field of the earth as additional zeitgeber for endogenous rhythms?" *Naturwissenschaften*, 71, 567–574), provides a "Zeitgeber" (time cue) for the synchronization of endogenous circadian rhythms in mammals and humans (Wever) (1968) "Einfluss schwacher elektro-magnetischer felder auf die circadiane Periodik des Menschen." *Naturwissenschaften*, 55, 29–32; Bliss and Heppner (1976) "Circadian activity rhythms influenced by near zero magnetic field." *Nature*, 261, 411–412). for instance, Wever (1968) "Einfluss schwacher elektromagnetischer felder auf die circadiane Periodik des Menschen." *Naturwissenschaften*, 55, 29–32) demonstrated that shielding of the ambient magnetic fields significantly desynchronized human circadian rhythms. Individuals placed in an underground bunker showed gradual desynchronization and lengthening of circadian rhythms, which could be resynchronized when an artificial 10-Hz, 25-mV/cm magnetic field was applied under similar conditions. Thus, it is thought that the circadian rhythmicity of the earth's magnetic field may have an additional "Zeitgeber" function in the organization of biological rhythms (Cremer-Bartels et al. (1984) "Magnetic field of the earth as additional zeitgeber for endogenous rhythms?" *Naturwissenschaften*, 71, 567–574). The effect of magnetic fields on human circadian rhythms is supported also by the observation in epileptic patients in whom treatment with picotesla range pulsed magnetic fields was shown to alter the circadian periodicity of seizures (Sandyk and Anninos (1992) "Magnetic fields alter the circadian periodicity of seizures." *International Journal of Neuroscience*, 63, 265–274).

The synchronizing effects of magnetic fields on circadian rhythms is mediated largely via the pineal gland which serves as a magnetoreceptor organ (Semm et al. (1980) "Effects of an earth-strength magnetic field on electrical activity of pineal cells." *Nature*, 288, 607–608; Semm (1983) "Neurobiological investigations on the magnetic sensitivity of the pineal gland in rodents and pigeons." *Comparative Biochemistry and Physiology*, 76A, 683–689; Olcese et al. (1988) "Geomagnetic field detection in rodents." *Life Sciences*, 42, 605–613; Welker et al. (1983) "Effects of an artificial magnetic field on serotonin N-acetyltransferase activity and melatonin content of the rat pineal gland." *Experimental Brain Research*, 50, 426–432). Experimental data indicate that exposure of animals and humans to magnetic fields is associated with a temporary inhibition of melatonin secretion (Welker et al. (1983) "Effects of an artificial magnetic field on serotonin N-acetyltransferase activity and melatonin content of the rat pineal gland." *Experimental Brain Research*, 50, 426–432; Wilson et al. (1986) "60-Hz electric-field effects on pineal melatonin rhythms: time course for onset and recovery." *Bioelectromagnetics*, 7, 239–242). However, with termination of magnetic fields exposure melatonin plasma levels usually return to their preexposure level and may even rise to higher levels over the following hours as shown by experiments performed by the inventor with subjects exposed nocturnally to picotesla range intensity magnetic fields (unpublished data). These changes in pineal melatonin functions in response to magnetic fields exposure are thought to induce significant biological effects through a process involving the synchronization of the biological rhythms including those of hormone release as well as neurotransmitter synthesis and release.

Since melatonin is a "master hormone" involved in the programming of the aging process and as aging is associated with pineal failure and administration of melatonin or pineal extracts prolongs life span in experimental animals, I believe that activation of the pineal gland by periodic application of pulsed magnetic fields may be used to retard the aging process and therapeutically to improve pathological states which are linked to or result from pineal failure due to aging such as sleep disturbances, loss of memory functions, disturbances of behavior, and depressive mood.

This is supported by the observations that pulsed magnetic fields have been shown in normal elderly subjects to alleviate the deleterious effects of jet-lag (i.e., fatigue, malaise), improve sleep efficiency, restore dream recall, increase level of energy and improve mood, promote relaxation, improve level of concentration, enhance sexual functions, improve bowel functions with resolution of constipation, normalize previously increased plasma levels of cholesterol, normalize previously elevated blood glucose levels, normalize previously elevated blood pressure, diminish the activity of psoriatic skin lesions, and enhance immune functions (i.e., prevent exacerbation of herpes infection; diminish frequency of influenza infections). The most dramatic effects of pulsed magnetic fields in normal adult and elderly subjects included improvement in sleep, mood, behavior (agitation and impulsive aggressive behavior), and short-term memory functions.

In patients with Parkinson's disease and Alzheimer's disease, which are both diseases of aging (Knoll (1990) "Nigrostriatal dopaminergic activity, deprenyl treatment and longevity." In Streifler et al. *"Advances in neurology: Parkinson's disease: anatomy, pathology and therapie."* New York: Raven Press; Langston (1988) "Aging, neurotoxins, and neurodegenerative disease." In R. D. Terry (Ed.), *Aging and the brain* (pp. 149–164). New York: Raven Press), application of AC pulsed magnetic fields once to twice per week has been shown to improve sleep efficiency, abolish nocturnal awakenings, restore dream recall, improve short-term memory functions, improve concentration and level of energy, restore alpha brain wave activity on the EEG record (which is diminished with aging), enhance sexual functions, improve gastrointestinal functions (i.e., constipation), diminish the extent of psoriatic skin lesions, normalize previously recorded high blood pressure, and increase plasma growth hormone, luteinizing hormone (LH) and testosterone levels (Sandyk (1992) "Weak magnetic fields in the treatment of Parkinson's disease with the "on-off" phenomenon." *International Journal of Neuroscience*, 66, 97–106; Sandyk and Derpapas (1993) "Further observations on the unique efficacy of picotesla magnetic fields in Parkinson's disease." *International Journal of Neuroscience*, 69, 167–183; Sandyk (1995) "Improvement in short-term visual memory by weak electromagnetic fields in Parkinson's disease." *International Journal of Neuroscience*, 81, 67–82; Sandyk and Derpapas (1993) "The effects of external picotesla range magnetic fields on the EEG in Parkinson's disease." *International Journal of Neuroscience*, 70, 85–96; Sandyk (1994) "A drug naive Parkinsonian patient successfully treated with electromagnetic fields." *International*

Journal of Neuroscience, 79, 99–110; Sandyk (1994) "Alzheimer's disease: Improvement of visual memory and visuoconstructive performance by treatment with picotesla range magnetic fields." *International Journal of Neuroscience*, 76, 185–225; Sandyk (1994) "The effects of external picotesla range magnetic fields on the EEG in Parkinson's disease: a follow up study." *International Journal of Neuroscience*, 76, 227–229), features which are consistent with the notion that pulsed magnetic fields improve age-related disturbances linked to pineal failure. These therapeutic effects appeared to be significantly augmented when pulsed magnetic fields were administered in conjunction with my pharmacological-nutritional composition described in my parent application Ser. No. 181,677 and my continuation-in-part thereof filed concurrently herewith (RS1). The use of my composition is important because the therapeutic efficacy of externally applied magnetic fields, as described in the prior art, is limited by several factors:

(a) The pineal gland tends to undergo an increased rate of calcification with age and particularly in association with various systemic disorders (Trentini et al. (1987) "Pineal calcification in different physiopathological conditions in humans." In Trentini et al. *Fundamentals and clinics in pineal research* (pp. 291–304) New York: Raven Press; Welsh (1985) "Pineal calcification: structural and functional aspects." *Pineal Research Reviews*, 3, 41–68). It is believed that calcification of the pineal gland may interfere with its magnetosensitivity. The calcified material which consists of hydroxyapatite and calcium carbonate apatite crystals as well as high concentrations of several trace elements such as iron, magnesium, zinc, copper, and manganese (Humbert and Pevet (1991) "Calcium content and concretions of pineal glands of young and old rats." *Cell and Tissue Research*, 263, 593–596) may alter the physicochemical properties of the gland and interfere with the ability of the pineal gland to release melatonin in response to magnetic fields;

(b) Reduction in the activity of the pineal gland in aging may be related to various factors including, among others, increased accumulation of aging pigment in the pinealocytes, decrease in pineal receptor sensitivity and/or density, decline in the availability of nutritional co-factors for serotonin and melatonin synthesis, decline in the capacity of pineal cells to synthesize serotonin from tryptophan, and decrease sympathetic nervous system activity which provides a stimulus for melatonin syntheses (Tang et al. (1985) "Aging and diurnal rhythms of pineal serotonin, 5-hydroxyindoleacetic acid, norepinephrine, dopamine and serum melatonin in the male rat." *Neuroendocrinology*, 40, 160–164; Dax and Sugen (1988) "Age-associated changes in pineal adrenergic receptors and melatonin synthesizing enzymes in the Whistar rat." *Journal of Neurochemistry*, 50, 468–472 Wildi and Frauchiger (1965) "Modifications histologiques de l'epiphyse humaine pendant l'enfance, l'age adulte et le vieillissement." *Progress in Brain Research*, 10, 218–233); and (c) Aging is associated with diminished serotonin receptor density and cerebral concentrations of serotonin, a precursor of melatonin synthesis. In addition, levels of the amino-acid tryptophan, a precursor of serotonin synthesis, are reduced in the blood of a proportion of elderly people who fail to absorb tryptophan (Ingram et al. (1982) "Circadian rhythmicity and sleep: effects of aging in laboratory animals." *Neurobiology of Aging*, 3, 287–297; Gottfries (1990) "Disturbance of the 5-hydroxytryptamine metabolism in brains from patients with Alzheimer's dementia." *Journal of Neural Transmission*, 30 (suppl) (33–43); Goldman-Rakic and Brown (1981) "Regional changes of monoamines in cerebral cortex and subcortical structures of aging rhesus monkeys." *Neuroscience*, 6, 177–187; Gross-Isseroff et al. (1990) "Autoradiographic analysis of age-dependent changes in serotonin 5-$HT_2$ receptors of the human brain postmortem." *Brain Research*, 519, 223–227; Chen Shih and Young (1978) "The alteration of serotonin binding sites in aged human brain." *Life Sciences*, 23, 1441–1448; Lehmann, (1979) "How to investigate malabsorption and the value of repeated tryptophan loads." In Schou, M. and Stromgren, E. (Eds.), *Origin, prevention and treatment of affective disorders* (pp. 125–138) London:Academic Press). Brain serotonin deficiency contributes to the development of sleep, mood and memory disturbances in the elderly. Moreover, many of the biological effects of melatonin are mediated via the serotonin system (Smith and Kappers (1975) "Effect of pinealectomy, gonadectomy, pCPA and pineal extracts on the rat parvocellular neurosecretory hypothalamic system: a fluorescence histochemical investigation." *Brain Research*, 86, 353–371; Anton-Tay et al. (1968) "Brain serotonin concentration: elevation following intraperitoneal administration of melatonin." *Science*, 162, 277–278; Anton-Tay (1974) "Melatonin:effect on brain function." *Advances in Biochemical Psychopharmacology*, 11, 315–324; Olcese (1985) "Enhancement of melatonin's antigonadal action by daily injections of the serotonin uptake inhibitor fluoxetine in male hamsters." *Journal of Neural Transmission*, 64, 151–161; Gaffori and Van Ree (1985) "Serotonin and antidepressant drugs antagonize melatonin-induced behavioral change after injection into the nucleus accumbens of rats." *Neuropharmacology*, 24, 237–244).

SUMMARY OF THE INVENTION

The present invention relates to the use of a pulsed magnetic field in combination with a pharmacological-nutritional composition to retard the aging process and improve age-related disease conditions. More particularly, the present invention relates to the enhancement of the activity of the pineal gland and specifically the production of its principal hormone melatonin which is considered a "master hormone" in the regulation of biological rhythms. The purpose of the composition is to sensitize the pineal gland to the effects of magnetic fields.

My invention includes a method of retarding the aging process and improving the symptoms of age-related disease conditions in humans which comprises administering to a human in need thereof an effective amount of a composition which increases serotonin transmission to such human followed by the application to the brain of the human of an effective amount of an AC pulsed magnetic field of proper intensity, frequency and waveform. This composition is preferably supplemented by a dietary composition rich in the amino-acid tryptophan. Optionally, my invention includes administering an effective amount of an agent which promotes growth hormone release prior to the application of the AC pulsed magnetic field. My invention also includes the above referred to composition for increasing serotonin transmission to humans, which composition may optionally include an effective amount of an agent which promotes growth hormone release.

DETAILED DESCRIPTION

Based on studies I have conducted in experimental animals, the data provided in the literature presented above and my medical experience treating elderly people, it appears that aging is related to a decline in pineal melatonin functions and serotonin neurotransmission and that several pathological conditions associated with aging such as sleep disorders, mood and conduct disturbances such as depression and aggressive behavior, decline in memory functions, rise in blood pressure, impairment of glucose tolerance and the like in elderly, are related to pineal failure which is part of the aging process. By periodically stimulating the pineal gland and increasing melatonin production using pulsed magnetic fields in the picotesla range intensity, I believe, based on my experience with elderly people, particularly patients with Parkinson's disease, Alzheimer's disease and multiple sclerosis, that one can retard the aging process and can improve conditions related to pineal failure such as sleep and mood disturbances as well as memory functions. To retard the aging process which is due to diminished pineal melatonin functions and reduced serotonin neurotransmission, application of an appropriate magnetic field once per week which should preferably consist of two successive AC pulses each of 10 to 15 minutes provides a significant improvement.

More enhanced results, however, are achieved according to my invention by the use of my novel pharmacological-nutritional composition which increases serotonin transmission together with the AC pulsed magnetic field as described in more detail herein. My composition comprises an effective amount of a serotonin precursor, an effective amount of a stimulant to facilitate the transport of a serotonin precursor into the brain, an effective amount of an agent to increase plasma tryptophan concentrations, an effective amount of a stimulant of serotonin synthesis, an effective amount of a stimulant of serotonin release and an effective amount of a stimulant of serotonin receptors, and is preferably supplemented by an effective amount of a dietary composition rich in the amino-acid tryptophan.

Plasma melatonin concentrations decline progressively with age with a steeper decline occurring in men at about the age of 50 years while in women a more dramatic decline occurs perimenopausally starting at the age of 45 years (Nair et al. (1986) "Plasma melatonin- an index of brain aging in humans?" *Biological Psychiatry*, 21, 141–150; Sack et al. (1986) "Human melatonin production decreases with age." *Journal of Pineal Research*, 3, 379–388). Consequently, it is advocated that the procedure to retard the aging process in men should begin at about the age of 50 while in women the procedure should begin earlier around the age of 45 years coincident with the fall of pineal melatonin production perimenopausally.

It is preferred for maximum effect that the AC pulsed magnetic field is applied to the brain of the human in two applications separated by an interval of time. Preferably the duration of the first AC pulsed magnetic field is 10 to 15 minutes. The duration of the second AC pulse is also preferably 10 to 15 minutes. It is preferred that the time delay between the application of the first AC pulse and the application of the second AC pulse is 15 to 30 minutes.

According to one embodiment of my invention, the composition comprises one or more of the following: an effective amount of a serotonin precursor, an effective amount of a stimulant to facilitate the transport of a serotonin precursor into the brain, an effective amount of an agent to increase plasma tryptophan concentrations, an effective amount of a stimulant of serotonin synthesis, an effective amount of a stimulant of serotonin release and an effective amount of a stimulant of serotonin receptors. The effective amount of a dietary composition rich in the amino-acid tryptophan is a preferred supplement to my composition and comprises including in the diet of the person to be treated various foods which are rich in tryptophan. My composition may optionally include an effective amount of an agent which promotes growth hormone release.

According to a further embodiment of the present invention, the serotonin precursor is L-tryptophan (L-TP)or L-5-hydroxytryptophan (L-5-HTP).Since serotonin present in the blood is excluded by the blood brain barrier from entry into the brain, the administration of precursors such as L-TP or L-5-HTP is used to increase brain concentrations of serotonin (Wurtman and Fernstrom (1975) "Control of brain monoamine synthesis by diet and plasma amino-acids." *The American Journal of Clinical Nutrition*, 28, 638–647).

According to a further embodiment of the present invention, the stimulant to facilitate the transport of a serotonin precursor into the brain is one which facilitates the transport of tryptophan into the brain. It is preferably vitamin $B_3$, chromium (preferably chromium picolinate) or a mixture thereof. Chromium is an essential co-factor for insulin production and action (Rabinowitz et al. (1983) "Effects of chromium and yeast supplements on carbohydrate and lipid metabolism in diabetic men." *Diabetes Care*, 6, 319–327). Insulin, in turn, facilitates the entry of tryptophan into the brain by inhibiting the uptake of the branched chain amino-acids leucine, isoleucine, and valine which compete with tryptophan for entry into the brain (Wurtman and Fernstrom (1976) "Control of brain neurotransmitter synthesis by precursor availability and nutritional state." *Biochemical Pharmacology*, 25, 1691–1696).

According to a further embodiment of the present invention the agent to increase plasma tryptophan concentrations is a salicylate. L-tryptophan is usually transported in the blood in a bound or complexed form with the protein albumin. It has been shown that various salicylates displace tryptophan from its protein binding site with albumin in blood plasma thereby raising the free or unbound tryptophan concentration in the blood. The bond-breaking effect exerted by salicylates on the binding of tryptophan to albumin causes a greater availability of free tryptophan for diffusion into the brain (Tagliamonte et al. (1973) "Increase of brain tryptophan and stimulation of serotonin synthesis by salicylate." *Journal of Neurochemistry*, 20, 909–912). While aspirin is the salicylate preferred, any other pharmaceutically acceptable salicylate such as sodium salicylate would serve as well.

According to a further embodiment of the present invention, the stimulant of serotonin synthesis is preferably vitamin $B_1$, vitamin $B_2$, vitamin $B_3$, vitamin $B_6$, biotin, S-adenosylmethionine, folic acid, ascorbic acid, magnesium, coenzyme $Q_{10}$, piracetam or mixtures of two or more thereof.

According to a further embodiment of the present invention, the stimulant of serotonin release is preferably fenfluramine (Fuller (1986) "Pharmacologic modification of serotonergic functions: drugs for the study and treatment of psychiatric and other disorders." *Journal of Clinical Psychiatry*, 47 (suppl 4), 4–8).

According to a further embodiment of the present invention, the stimulant of serotonin receptors is preferably ergoloid mesylates (Hydergine®). Hydergine® has been shown to improve mental alertness and memory functions in normal subjects and those with organic mental deterioration an effect which is related partly to its stimulating properties of serotonin receptors in the brainstem reticular formation (Depoortere et al. (1975) "Neuropharmacological studies on Hydergine." *Triangle*, 14, 73–79).

According to a further embodiment of the present invention, the dietary composition should include foods which are rich in the amino-acid tryptophan such as turkey (4 ounces twice a week), milk (8 ounces per day of whole, low-fat, or skim), bananas (1 per day), nuts (1–2 ounces per day) and dry-roasted sunflower seeds (3–4 ounces per day).

I prefer the use of L-arginine or L-ornithine as agents to promote growth hormone release. Preferably, these agents would be administered the night before and most preferably one to two hour prior to the application of the AC pulsed magnetic field.

It is preferred that the intensity of the magnetic field be in the range of 7.5–75 picotesla. The magnetic field is a time varying field with a wave form which is sinusoidal, triangular, trapezoidal, square or a composite thereof.

It is preferred that the patient's eyes be shielded during the application of the AC pulsed magnetic fields. The fields are preferably applied to the subject's head using a helmet-like transducer array. The helmet-like transducer array preferably comprises an array of coils which are flat or helical.

It is preferred that the AC magnetic field frequency is 5 Hz–8 Hz.

For the retardation of the aging process resulting from diminished pineal melatonin functions and reduced serotonin neurotransmission, it is preferred that the AC pulsed magnetic field is applied to the human head once per week.

To improve disorders of sleep, mood, behavior, and memory functions, it is preferred that the AC pulsed magnetic field is applied to the human head once or twice per week.

For the treatment of hypertension, it is preferred that the AC pulsed magnetic field is applied once or twice per week to the human head.

For the treatment of hypercholesterolemia, it is preferred that the AC pulsed magnetic field is applied to the human head once or twice per week.

For the treatment of glucose intolerance and overt diabetes mellitus, it is preferred that the AC pulsed magnetic field is applied to the human head once or twice per week.

For the treatment of loss or diminished libido, it is preferred that the AC pulsed magnetic field is applied to the human head once or twice per week.

For the treatment of bowel constipation, it is preferred that the AC pulsed magnetic field is applied to the human head once or twice per week.

For the treatment of psoriasis vulgaris including psoriatic arthropathy, it is preferred that the AC pulsed magnetic field is applied to the human head once or twice per week.

For the treatment of osteoarthritis, it is preferred that the AC pulsed magnetic field is applied once or twice per week.

For the treatment of osteoporosis, it is preferred that the AC pulsed magnetic field is applied once or twice per week.

For the treatment of prostate hypertrophy, it is preferred that the AC pulsed magnetic field is applied once or twice per week.

When an effective amount of an agent which promotes growth hormone release is administered, it is administered prior to application of the AC pulsed magnetic field. Preferred agents are L-arginine or L-ornithine. The agent is preferably administered the night before preferably one to two hours prior to the application of the AC pulsed magnetic field.

It is also preferred that the composition be administered four to eight weeks before the application of the first AC pulsed magnetic field.

It is preferred that the AC pulsed magnetic field is a time-varying field with a waveform which is sinusoidal, triangular, trapezoidal, square or a composite thereof. It is also preferable that the subject's eyes are shielded during the application of each AC pulsed magnetic field. The fields may be applied to the subject's head using a helmet-like transducer array as illustrated in the drawings. The helmet-like transducer array preferably comprises an array of coils which are flat, i.e. two dimensional or helical, i.e. three dimensional.

I find particularly good results achieved according to my invention when the AC pulsed magnetic field is applied at night, preferably after 8:00 p.m. I believe this is because plasma melatonin levels begin to rise after about 8:00 p.m. reaching a peak between midnight and 2:00 a.m. (Waldhauser et al. (1984) "Melatonin in human body fluids: clinical significance" In Reiter, R. J. (Ed.), *The pineal gland* (pp. 345–370) New York: Raven Press). Since pulsed magnetic fields alter circadian melatonin secretion, the optimal response to the magnetic field would be expected to occur at night, the time the pineal gland is maximally active.

My composition which is useful for retarding the aging process and improving age-related disease conditions in humans when administered to a human followed by the application to the brain of the human of an effective amount of an AC pulsed magnetic field of proper intensity, frequency and waveform comprises an effective amount of a composition which increases serotonin transmission to the human and may optionally include an effective amount of an agent which promotes growth hormone release.

According to one embodiment, my composition comprises one or more of the following: an effective amount of a serotonin precursor, an effective amount of a stimulant to facilitate the transport of a serotonin precursor into the brain, an effective amount of an agent to increase plasma tryptophan concentrations, an effective amount of a stimulant of serotonin synthesis, an effective amount of a stimulant of serotonin release and an effective amount of a stimulant of serotonin receptors.

Preferably, the serotonin precursor is L-tryptophan or L-5-hydroxytryptophan.

Preferably, the stimulant to facilitate the transport of a serotonin precursor into the brain is vitamin $B_3$, chromium or a mixture thereof.

Preferably, the agent to increase plasma tryptophan concentration is a salicylate.

Preferably, the stimulant of serotonin synthesis is vitamin $B_1$, vitamin $B_2$, vitamin $B_3$, vitamin $B_6$, biotin, S-adenosylmethionine, folic acid, ascorbic acid, magnesium, coenzyme $Q_{10}$, piracetam or mixtures of two or more thereof.

Preferably, the stimulant of serotonin release is fenfluramine.

Preferably, the stimulant of serotonin receptors is an ergoloid mesylate.

DETAILED DESCRIPTION

According to my present invention, the treatment procedure which I have found to be most effective is when the patient is given my composition supplemented by the dietary composition, beginning 4–8 weeks, preferably 6–8 weeks, prior to the application of the first AC pulsed magnetic field which pulsed magnetic field is preferably applied in two treatments.

In the initial treatment phase, the patient is given the composition which comprises the stimulants to facilitate the transport of the serotonin precursor into the brain, an agent which increases plasma tryptophan concentrations, the composition comprising the stimulants of serotonin synthesis, the stimulant of serotonin receptors, and the dietary composition rich in the amino-acid tryptophan.

On the night prior to application of the magnetic fields the subject is given a serotonin precursor to augment the synthesis of serotonin and melatonin and an agent to promote the release of growth hormone. For the purpose of increasing serotonin synthesis the inventor recommends a preparation containing the essential amino-acid tryptophan to be taken at bedtime (L-tryptophan 500 mg–3 g, orally) or a preparation containing L-5-hydroxytryptophan (L-5-HTP) (25–50 mg, orally) taken at bedtime. L-tryptophan is the preferred serotonin precursor due to its low side effect profile and low risk of toxicity (Young (1986) "The clinical psychopharmacology of tryptophan." In Wurtman, R. J. and Wurtman, J. J. (Eds.), Nutrition and the brain (pp. 49–88), vol. 7. New York: Raven Press). For the purpose of promoting growth hormone release the inventor uses L-arginine or L-ornithine (500 mg–1,000 mg) to be taken at bedtime.

One to two hours prior to application of the first magnetic treatment the patient is given a stimulant of serotonin release. For this purpose the inventor uses the drug fenfluramine hydrochloride (Pondimin®; 10–20 mg, orally). In addition, the subject is given again an agent to promote the release of growth hormone such as L-arginine or L-ornithine (500 mg–1,000 mg).

The first magnetic pulse is given for a period of 10–15 minutes using an AC frequency of 5 Hz–7 Hz preferably an AC frequency of 5 Hz. After a break of 15–30 minutes, a second magnetic pulse is applied for a period of 10–15 minutes using a higher AC frequency of 7 Hz–8 Hz. It is my experience that the application of the second AC pulse is extremely beneficial for the treatment of neurological and mental disorders and it is therefore preferred to use a second pulse also in the case where the treatment procedure is applied for retardation of the aging process and for the treatment of age-related disease conditions.

Best results are obtained when the AC pulsed magnetic field is administered at night, preferably after 8:00 p.m.

The AC pulsed magnetic fields are preferably applied via an external magnetic coil assembly, or transducer. The transducer is constructed of flexible substrate which allows the transducer to be bent and positioned on the head of a patient in the form of a helmet. The transducer is constructed of a set of coils positioned side-by-side in a two-dimensional array. In the preferred embodiment of the invention as shown in FIGS. 1–4, the transducer is constructed of 16 coils arranged in a matrix of four rows by four columns, and the area of each coil is preferably 3.14 $cm^2$. When these coils are carrying an electric current, they produce magnetic fields with lines of force parallel to the axes of the respective coils. The locations of the coils are such that the resultant magnetic fields are uniform. The produced magnetic fields are alternating and their intensity can be less than approximately 60 microtesla. For therapeutic purposes herein, it is preferred to employ magnetic fields strength in the range of 7.5 to 75 picotesla with an AC frequency in the range of 5 Hz–8 Hz. In the experience of the inventor higher amplitudes of the exposed magnetic fields above 75 picotesla and up to 1,000 picotesla did not provide an additional benefit for patients with neurological and mental disorders and it is believed that amplitudes above 75 picotesla will not provide an additional benefit also for subjects undergoing this treatment procedure for retardation of the aging process and for the treatment of age-related disease conditions.

To maintain the effects of the treatment, "maintenance therapy" is implemented during which time the procedure is repeated once to twice per week. During the period of "maintenance therapy" the subject continues to take the pharmacological-nutritional composition except for the compositions which are administered the night before (i.e., L-tryptophan and L-arginine) and just prior to the application of magnetic fields (i.e., fenfluramine and L-arginine). It is recommended that during the period of "maintenance therapy" the subject should spend at least one hour daily outdoors to maximize sunlight exposure to enhance serotonin functions and synchronize melatonin circadian rhythms (Wurtman and Wurtman (1989) "Carbohydrates and depression." Scientific American, January, 68–75). During the "maintenance therapy" the subject may continue to receive medications for his/her particular disease. For instance, in the case of hypercholesterolemia the subject may continue to use his cholesterol lowering drugs while receiving the composition and the magnetic field therapy. In some instances, such as in the case where this treatment procedure produced normalization of blood pressure antihypertensive drugs may be reduced or discontinued based on prior consultation with a physician.

With reference to FIGS. 1–4, there is shown a transducer 30 which is employed in the practice of the invention to apply magnetic fields upon the brain of a patient. The transducer 30 comprises a set of coils 32, and is placed on the head of a patient 34. Upon energization of the coils 32 with electric current, the coils 32 produce magnetic fields which are directed into the brain, and particularly into the area of the pineal gland, of the patient 34. The patient 34 holds a cup 36 to demonstrate the inventive feature of ingesting various pharmacological and nutritional components of the composition prior to application of the magnetic fields. Electric current is applied to the coils 32 by a driver 38, the driver 38 including a voltage generator 40 and an output resistor 42 by which the generator 40 is coupled to the coils 32. Also included in the driver 38 is a timer 44 for activating the generator 40 to provide a sequence of pulses of output voltage which are applied to the resistor 42. The resistor 42 has a resistance of approximately 0.5 megohm in the preferred embodiment of the invention, and the coils 32 are connected in series to provide a total resistance of approximately one ohm between the terminals 46 and 48 of the transducer 30. A volt meter 50 is connected between output terminals 52 and 54 of the generator 40 to provide an indication of the magnitude of the output voltage of the generator 40.

Figure 1:
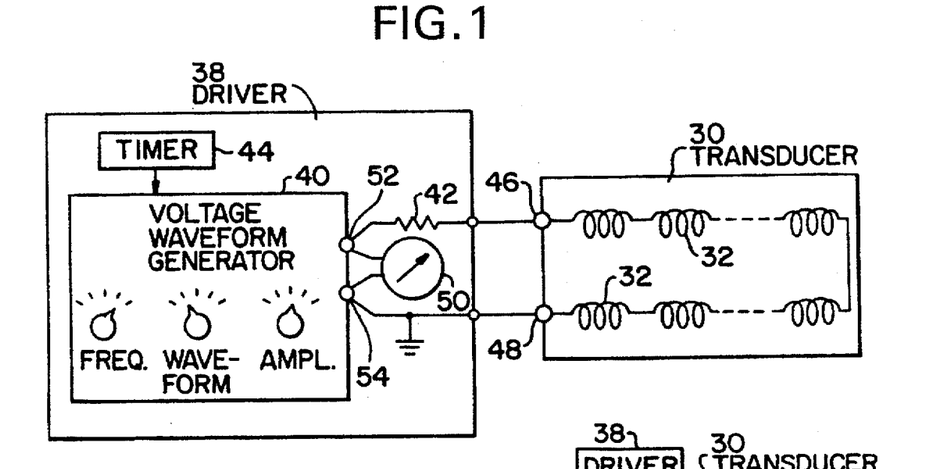
FIG. 1 is a schematic diagram showing connections of a signal generator to an array of coils for applying AC pulsed magnetic fields to a patient's head.
Figure 2:
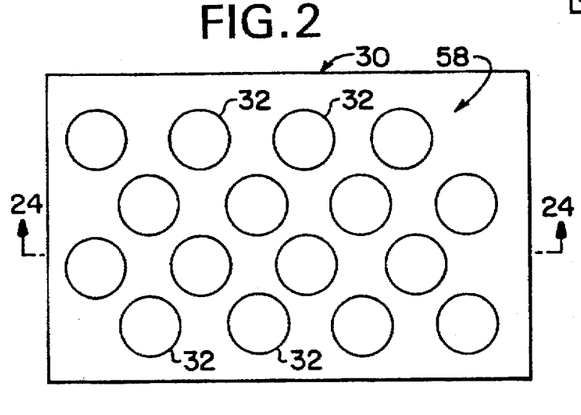
FIG. 2 and 2A show plane views of alternate configurations of the array of coils.
Figure 2A:
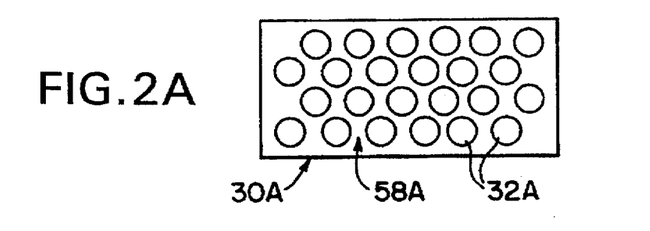
Figure 3:
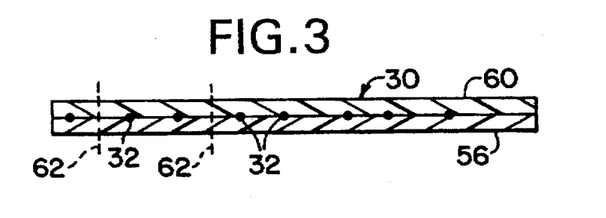
FIG. 3 is a sectional view of the array of coils taken along the line 24—24 line in FIG. 1.
Figure 4:
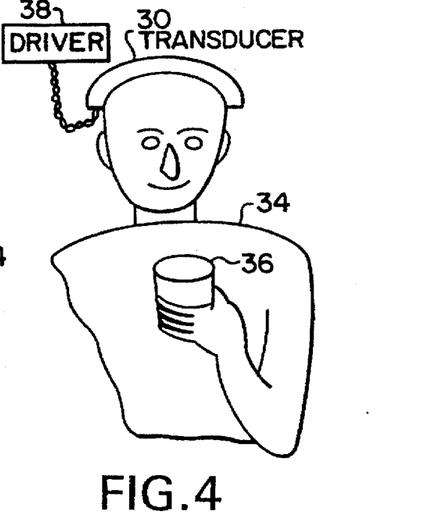
FIG. 4, is a stylized view showing emplacement of the array of coils upon a patient's head for applying the magnetic fields to the patient's head.

The coils 32 and the resistor 42 constitute a series circuit between the terminals 52 and 54 of the generator 40. Since the internal impedance of the driver 38, as provided by the resistor 42, is several orders of magnitude greater than that of the transducer 30, the voltage generator 40 in combination with the resistor 42 acts as a current source to provide a current to the transducer 30 proportional to the voltage outputted by the generator 40. In view of the current-source function of the driver 38, the meter 50 also provides an indication of the magnitude of the current flow in the coils 32 of the transducer 30. The intensity of the magnetic fields produced by the current in the coils 32 is proportional to the magnitude of the current and, accordingly, the reading of the meter 50 serves also as an indication of the intensity of the magnetic fields applied by the transducer 30 to the patient 34. The generator 40 is of well-known construction and provides a voltage with a periodic waveform. The generator 40 includes controls for selecting the AC frequency of the voltage, the waveform of the voltage, and the amplitude of the voltage. By way of example, the voltage may be a steady DC voltage, or may be varied in frequency over a range of 0.1 Hz to 10,000 Hz. The waveform may be sinusoidal, triangular, trapezoidal, square or a combination of more than one of these waveforms such as the sum of square plus sinusoid as shown in FIG. 5, by way of example.

The transducer 30 comprises a substrate 56 which supports the coils 32 in their respective positions in a two-dimensional array 58. By way of example in the practice of the invention, in one embodiment of transducer 30, the array 58 has a total of 16 of the coils 32 arranged in four rows, each of the rows having four of the coils 32, as shown in FIG. 5. Each coil 32 has, typically four or five turns, and has a diameter of approximately two centimeters, with an area of approximately three square centimeters. In a second embodiment of the transducer 30A, there is array 58A of the coils 32A having a total of 24 coils arranged in four rows each having six coils 32A, as shown in FIG. 5A. A cover layer 60 is disposed on top of the substrate 56 and the coils 32. The substrate 56 and the cover layer 60 are formed of a flexible electrically-insulating plastic material which permits flexing of the transducer 30 to conform to the curvature of the subject's head. The coils 32 are formed of a flexible electrically-conductive material such as copper which permits the foregoing flexing of the transducer 30.

In the case of energization of the coils 32 with a sinusoidal current, the generator 40 is operated to output a peak voltage, typically, of four volts relative to ground. This voltage provides a peak current of eight microamperes which is more than enough current to provide a peak magnetic field intensity of 60 picotesla. The output voltage of the generator 40 is adjusted to provide a desired intensity to the resultant alternating magnetic fields. If desired, the resistance of the resistor 42 may be reduced to provide still larger values of current for greater intensity of magnetic fields. Upon energization of the coils 32 with electric current, the resultant magnetic fields have lines of force parallel to the axes 62 of the respective coils 32. The locations of the coils 32 provide that the resultant magnetic fields are uniform. The driver 38 and the transducer 30 or 30A are capable of providing alternating magnetic fields in a frequency range of 0.1 Hz to 10 KHz, and intensity up to 60 microtesla. Typically, in the practice of the invention, the intensity of the alternating magnetic fields is in the range of 7.5 to 75 picotesla, and the frequency is in the range of 5 Hz–8 Hz.

Figure 5:
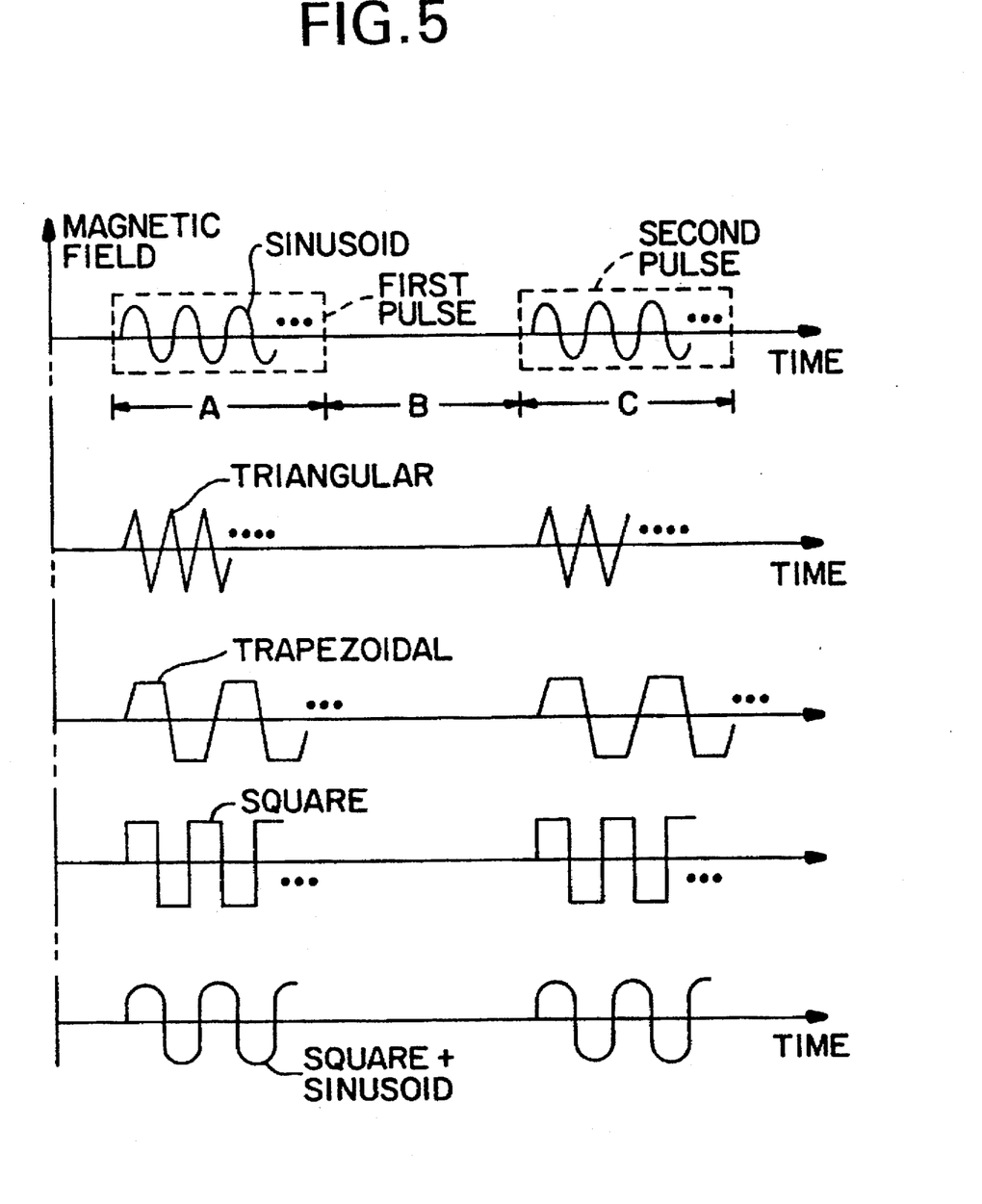
FIG. 5 is a diagram showing pulsation of the magnetic fields.

FIG. 5 shows a sequence of two pulses of magnetic fields wherein the direction and amplitude of the magnetic fields alternate in sinusoidal fashion. The sinusoidal form of the alternating magnetic fields is employed in the preferred embodiment of the invention. However, it is understood that some other waveform such as the aforementioned triangular or trapezoidal or square waveform may be used if desired. For example, in the case of the trapezoidal waveform, the rise and the fall times of the waveform together may occupy from 20% to 40% of each period of the waveform. Within each pulse, the AC frequency is held constant in the preferred embodiment of the invention. However, if desired, the AC frequency may be altered, as by a frequency ramp wherein the frequency increases during the pulse, such that the end frequency is greater than the initial frequency by 10%–30%.

FIG. 5 also shows the duration, A, of the first AC pulse, and the duration, B, of a rest interval or break between the AC pulses, and the duration, C, of the second AC pulse.

The transmission of signals in the nervous system is such that within the neuron (nerve cell) transmission is accomplished by propagation of an electrical signal while between neurons signal propagation is accomplished via the mediation of a neurotransmitter. A neurotransmitter is a molecule, such as a molecule of serotonin, dopamine, acetylcholine, and histamine, or other neurotransmitter by way of example. During the propagation of an electrical signal the neurotransmitter is released from the transmitter neuron ("presynaptic neuron") into the synaptic cleft from which it diffuses across the synaptic cleft to reach specific receptors in the receiving neuron ("postsynaptic neuron"). Activation of these receptors at the postsynaptic neuron causes either excitation or inhibition of the postsynaptic neuron. The transmitter neuron and the receiving receptor at the postsynaptic neuron are specific to only one type of neurotransmitter so that a plurality of different forms of the neuron transmitter/receptor allow for transmission of different forms of signals by respective ones of the neurotransmitter.

Neurotransmitters are produced in numerous locations throughout the nervous system. For instance, serotonin is produced in neurons that originate in the median raphe of the brainstem and which project to numerous brain areas including the spinal cord, cerebellum, hypothalamus, limbic system, and cortex. In the central nervous system serotonin affects mood, sleep and arousal, satiety, emesis, cardiovascular regulation, temperature control, pain, sedation, anxiety and depression. In the peripheral nervous system, the primary actions of serotonin are on the gastrointestinal tract and cardiovascular system, but it also affects the respiratory tract and genito-urinary system.

What is claimed is:

1. A method of ameliorating age-related disease conditions associated with or related pathogenetically to deficient serotonin neurotransmission and pineal functions in humans which comprises administering to a human in need thereof an effective amount of a composition which increases serotonin neurotransmission to said human followed by the application to the brain of the human of an effective amount of an AC pulsed magnetic field of proper intensity, frequency and waveform.

2. A method according to claim 1 wherein the AC pulsed magnetic field is applied to the brain of the human in two applications, separated by an interval of time.

3. A method according to claim 1 wherein the composition comprises one or more of the following: an effective amount of a serotonin precursor, an effective amount of a stimulant to facilitate the transport of a serotonin precursor into the brain, an effective amount of a stimulant to increase plasma tryptophan concentrations, an effective amount of a stimulant of serotonin synthesis, an effective amount of a stimulant of serotonin release and an effective amount of a stimulant of serotonin receptors, and is supplemented by an effective amount of a dietary composition rich in the amino-acid tryptophan.

4. A method according to claim 2 wherein the duration of the first AC pulsed magnetic field is 10–15 minutes.

5. A method according to claim 2 wherein the time delay between the application of the first AC pulsed magnetic field and the second AC pulsed magnetic field is 15–30 minutes.

6. A method according to claim 2 wherein the duration of the second AC pulsed magnetic field is 10–15 minutes.

7. A method according to claim 1 wherein the AC frequency is 5–8 Hz.

8. A method according to claim 1 wherein the AC pulsed magnetic field is applied once per week.

9. A method according to claim 7 to improve age-related disorders of sleep, mood, behavior, and memory functions wherein the AC pulsed magnetic field is applied once or twice per week.

10. A method according to claim 7 for the treatment of hypertension wherein the AC pulsed magnetic field is applied once or twice per week.

11. A method according to claim 7 for the treatment of hypercholesterolemia wherein the AC pulsed magnetic field is applied once or twice per week.

12. A method according to claim 7 for the treatment of glucose intolerance and overt diabetes mellitus wherein the AC pulsed magnetic field is applied once or twice per week.

13. A method according to claim 7 for the treatment of loss or diminished libido wherein the AC pulsed magnetic field is applied once or twice per week.

14. A method according to claim 7 for the treatment of bowel constipation wherein the AC pulsed magnetic field is applied once or twice per week.

15. A method according to claim 7 for the treatment of psoriasis vulgaris including psoriatic arthropathy wherein the AC pulsed magnetic field is applied once or twice per week.

16. A method according to claim 7 for the treatment of osteoarthritis wherein the AC pulsed magnetic field is applied once or twice per week.

17. A method according to claim 7 for the treatment of osteoporosis wherein the AC pulsed magnetic field is applied once to twice per week.

18. A method according to claim 7 for the treatment of prostate hypertrophy wherein the AC pulsed magnetic field is applied once to twice per week.

19. A method according to claim 1 which additionally comprises administering an effective amount of an agent which stimulates growth hormone release prior to application of the first AC pulsed magnetic field.

20. A method according to claim 19 wherein the agent is L-arginine or L-ornithine.

21. A method according to claim 19 wherein the agent is administered one to two hours prior to the application of the AC pulsed magnetic field.

22. A method according to claim 1 wherein the composition is administered four to eight weeks before the application of the first AC pulsed magnetic field.

23. A method according to claim 1 wherein the AC pulsed magnetic field is a time varying field with a waveform which is sinusoidal, triangular, trapezoidal, square or a composite thereof.

24. A method according to claim 1 wherein the patient's eyes are shielded during the application of each AC pulsed magnetic field.

25. A method according to claim 1 wherein the magnetic fields are applied to the head using a helmet-like transducer array.

26. A method according to claim 25 wherein the helmet-like transducer array comprises an array of coils which are flat or helical.

27. A method according to claim 1 wherein the AC pulsed magnetic field is applied at night.

28. A method according to claim 23 wherein the application is after 8:00 p.m.

29. A method according to claim 1 which includes the serotonin precursor which is L-tryptophan or L-5-hydroxytryptophan.

30. A method according to claim 1 which includes the stimulant to facilitate the transport of a serotonin precursor into the brain which is vitamin $B_3$, chromium or a mixture thereof.

31. A method according to claim 1 which includes the stimulant to increase plasma tryptophan concentrations which is a salicylate.

32. A method according to claim 1 which includes the stimulant of serotonin synthesis which is vitamin $B_1$, vitamin $B_2$, vitamin $B_3$, vitamin $B_6$, biotin, S-adenosylmethionine, folic acid, ascorbic acid, magnesium, coenzyme $Q_{10}$, piracetam, or mixtures of two or more thereof.

33. A method according to claim 1 which includes the stimulant of serotonin release which is fenfluramine.

34. A method according to claim 1 which includes the stimulant of serotonin receptors which is an ergoloid mesylate.

35. A method according to claim 1 wherein the dietary composition rich in the amino-acid tryptophan includes one or more of the following: turkey, milk, bananas, nuts and dry-roasted sunflower seeds.

36. A method according to claim 1 wherein the composition additionally comprises an effective amount of an agent which promotes growth hormone release.

37. A method according to claim 36 wherein the agent is L-arginine or L-ornithine.

38. A method according to claim 1, wherein the composition comprises an effective amount of a serotonin precursor, an effective amount of a stimulant to increase plasma tryptophan concentrations, an effective amount of a stimulant to facilitate the transport of tryptophan into the brain of the human, an effective amount of a stimulant of serotonin synthesis, an effective amount of a serotonin reuptake inhibitor, an effective amount of a stimulant of serotonin release and an effective amount of a stimulant of serotonin receptors.

39. A method according to claim 38, wherein the serotonin precursor is L-tryptophan or L-5-hydroxytryptophan; the stimulant to increase plasma tryptophan concentrations is a salicylate; the stimulant to facilitate the transport of tryptophan into the brain is vitamin $B_3$ or chromium; the stimulant of serotonin synthesis is vitamin $B_1$, vitamin $B_3$, vitamin $B_6$, biotin, S-adenosylmethionine, folic acid, ascorbic acid, magnesium, coenzyme $Q_{10}$, or piracetam; the serotonin reuptake inhibitor is sertraline, nefazodone, or trazodone; the stimulant of serotonin release is fenfluramine; and the stimulant of serotonin receptor is ergoloid mesylate, pergolide mesylate, or buspirone.

* * * * *